United States Patent [19]
Valan

[11] 3,954,960
[45] May 4, 1976

[54] HAIR AND SIMILAR COSMETIC PREPARATIONS CONTAINING A QUATERNIZED COPOLYMER OF VINYL PYRROLIDONE

[75] Inventor: Kent J. Valan, Easton, Pa.

[73] Assignee: GAF Corporation, New York, N.Y.

[22] Filed: June 29, 1973

[21] Appl. No.: 374,926

Related U.S. Application Data

[63] Continuation of Ser. No. 7,249, Jan. 30, 1970, abandoned.

[52] U.S. Cl. ............................ 424/47; 424/70; 424/71; 424/78; 424/358
[51] Int. Cl.² ........................................ A61K 7/00
[58] Field of Search ............... 424/71, 47, 78, 70; 260/86.1 N, 80.72

[56] References Cited
UNITED STATES PATENTS

| | | | |
|---|---|---|---|
| 3,385,839 | 5/1968 | Honig et al. | 260/80.73 |
| 3,634,368 | 1/1972 | Palmer | 260/80.72 |

*Primary Examiner*—Frederick E. Waddell
*Attorney, Agent, or Firm*—Walter C. Kehm; James N. Blauvelt

[57] ABSTRACT

Hair and similar cosmetic preparations, i.e., aerosol hair sprays, hair conditioners, and hair setting lotions, etc. containing as the film-forming resin a quaternized copolymer of vinyl pyrrolidone and a copolymerizable vinyl monomer, i. e., a di-loweralkylaminoalkyl (or hydroxy alkyl) acrylate or methacrylate. Such compositions containing the quaternized copolymer exhibit excellent adhesion and holding power when employed for hair care preparations.

13 Claims, No Drawings

HAIR AND SIMILAR COSMETIC PREPARATIONS CONTAINING A QUATERNIZED COPOLYMER OF VINYL PYRROLIDONE

This is a continuation of application Ser. No. 7249, filed Jan. 30, 1970 and now abandoned.

The present invention is directed to certain novel cosmetic compositions, i.e., aerosol hair sprays, hair conditioners, and hair setting lotions, creams, etc., containing a quaternary copolymer of vinyl pyrrolidone; more particularly, the present invention is directed to such cosmetic compositions containing the quaternary copolymers of vinyl pyrrolidone and a further copolymerizable vinyl monomer, such copolymers providing greater adhesion, greater holding power, and less flaking than conventional synthetic polymers used in hair and similar cosmetic preparations.

A number of synthetic polymers are presently used in hair sprays, hair wave set lotions, hair conditions, etc., the function of such synthetic polymers being generally to contribute "body" and holding power to the hair-do sets. The holding phenomena of hair sprays and setting lotions are, however, not very well defined. In this regard, in hair sprays a polymer globule holds several keratin fibers together so as to produce the necessary holding of the hair in place. In setting and conditioning lotions, however, polymers are deposited over the surface of the hair and again several hair strands are adhered together. In both cases it can be seen that polymer adhesion to the hair is a very important factor which influences the usefulness of a particular synthetic polymer or resin in a hair preparation. In this regard, many of the currently employed synthetic polymers or resins exhibited poor adhesion thereby causing poor holding of the hair in place and excessive flaking when the hair is combed or brushed.

At the present time the principal synthetic polymers or resins employed in hair sprays, wave set lotions, and hair conditioners include polyvinyl pyrrolidone homopolymers and copolymers, half esters of polyvinyl ethers - maleic anhydride, polyvinyl acetate - crotonic acid co- and terpolymers, half esters of ethylene - maleic anhydride as well as various others. With the exception of vinyl pyrrolidone homopolymers, all of the above conventionally employed synthetic polymers and resins used in hair sprays, wave set lotions, and hair conditioners give stiff hair-dos, thereby causing an unnatural look. In addition, such synthetic polymers or resins sometimes result in excessive flaking or excessive fly-away, thereby making preparations containing same unsatisfactory from a commercial standpoint.

Although polyvinyl pyrrolidone homopolymers provide a more natural look in that the same are free from some of the disadvantages of other commercially available products, the use of such homopolymer does not provide satisfactory holding of the hair at high humidity levels. Accordingly, this is one disadvantage of the use of polyvinyl pyrrolidone homopolymers in hair spray, wave set lotions and hair conditioner compositions which has created the desire and necessity for the development of further synthetic polymers and resins free from all of the above recited disadvantages. This has now been accomplished in accordance with the present invention.

Thus, briefly stated, it has been discovered in accordance with the present invention that the above disadvantages and inherent deficiencies of previously employed cosmetic compositions have been eliminated by the use of a new type of polymer or resin useful in hair setting compositions including aerosol hair sprays, hair conditioners and hair setting lotions and creams. Thus, it has been discovered in accordance with the present invention that certain quaternary derivatives of N-vinyl pyrrolidone copolymers are particularly useful in cosmetic compositions in that such polymers provide excellent holding power and contribute to excellent body without possessing the disadvantages of flaking and stiffening associated with previously employed polymer materials.

Accordingly, it is a principal object of the present invention to provide novel cosmetic compositions which are free from the inherent deficiencies and disadvantages of previously employed compositions, particularly hair care preparations.

It is a further object of the present invention to provide such compositions, e.g., hair spray compositions, which contain a quaternary copolymer of vinyl pyrrolidone, which contributes to the body and holding of the hair-do while eliminating the disadvantages of flaking and undue stiffness.

It is still a further object of the present invention to provide such novel compositions comprising a quaternary copolymer of N-vinyl pyrrolidone and a diloweralkylaminoalkyl (or hydroxyalkyl) acrylate or methacrylate and optionally a further copolymerizable vinyl monomer in a suitable cosmetic vehicle, e.g., water, alcohol or water-alcohol mixtures.

Still further objects and advantages of the novel compositions of the present invention will become more apparent from the following more detailed description thereof.

The above objects and advantages of the novel cosmetic compositions of the present invention are achieved by employing as the film-forming resin within such composition a quaternized derivative of a copolymer of N-vinyl pyrrolidone. In hair compositions, for example, such quaternary copolymers exhibit improved substantivity to the hair; by this it is meant, that such polymeric materials are adsorbed onto the keratin surface, thereby improving hair strength and increasing hair weight. Furthermore, such adsorption of the quaternary copolymers employed in the novel compositions of the present invention is more uniform and more continuous than the absorption that can be obtained with currently available hair setting resins. Accordingly, this provides for a distinct advantage associated with the particular compositions of the present invention when compared, for example, with conventional prior art compositions.

The quaternary copolymers employed in the novel compositions of the present invention are those which have the following formula:

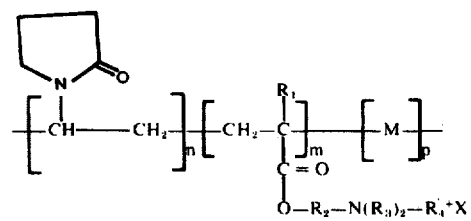

wherein $n$ represents 40 – 90 mole percent, $m$ is 5 – 40 mole percent, $p$ is from 0 – 50 mole percent, and $n+m+p = 100$; $R_1$ is H or $CH_3$; $R_2$ is $$CH_2CH-CH_2$$
$$\phantom{CH_2CH-}|$$
$$\phantom{CH_2CH-}OH$$

or $C_xH_{2x}$ where $x = 2-18$; $R_3$ is $CH_3$ or $C_2H_5$; $R_4$ is $CH_3$, $C_2H_5$, 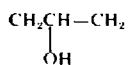; X is Cl, Br, I, $SO_4$, X is Cl, Br, I, $SO_4$, $HSO_4$, $CH_3SO_3$; and M is a monomeric unit resulting from the heteropolymerization employing an optional copolymerizable vinyl monomer.

As indicated from the above formula, such quaternary copolymers are prepared by the copolymerization of N-vinyl pyrrolidone and di-loweralkylaminoalkyl (or hydroxy alkyl) acrylate or methacrylate, and optionally a further copolymerizable vinyl monomer. The monomers are copolymerized in accordance with the present invention so that based upon 100 mole percent, the vinyl pyrrolidone units are present in an amount of 40 –'90 mole percent, the units derived from the di-loweralkylaminoalkyl (or hydroxy alkyl) acrylate or methacrylate constitute from 5 to 40 mole percent, and the units derived from the further copolymerizable vinyl monomer constitute from 0 to 5 mole percent.

Exemplary di-loweralkylaminoalkyl (or hydroxy alkyl) acrylates or methacrylates suitably employed in the production of the quaternary copolymers of the present invention include such materials as:

dimethylaminomethyl acrylate
dimethylaminomethyl methacrylate
diethylaminomethyl acrylate
diethylaminomethyl methacrylate
dimethylaminoethyl acrylate
dimethylaminoethyl methacrylate
dimethylamino-2-hydroxy propyl acrylate
dimethylamino-2-hydroxy propyl methacrylate
diethylamino-2-hydroxy ethyl acrylate
diethylamino-2-hydroxy ethyl methacrylate
dimethylaminobutyl acrylate
dimethylaminobutyl methacrylate
dimethylaminoamyl methacrylate
diethylaminoamyl methacrylate
dimethylaminohexyl acrylate
diethylaminohexyl methacrylate
dimethylaminooctyl acrylate
dimethylaminooctyl methacrylate
diethylaminooctyl acrylate
diethylaminooctyl methacrylate
dimethylaminodecyl methacrylate
dimethylaminododecyl methacrylate
diethylaminolauryl acrylate
diethylaminolauryl methacrylate
dimethylaminostearyl acrylate
dimethylaminostearyl methacrylate
diethylaminostearyl acrylate
diethylaminostearyl methacrylate
etc.

The optional vinyl monomer represented by M in the above structural formula can comprise any conventional vinyl monomer copolymerizable with N-vinyl pyrrolidone. Thus, for example, suitable conventional vinyl monomers include the alkyl vinyl ethers, e.g., methyl vinyl ether, ethyl vinyl ether, octyl vinyl ether, etc.; acrylic and methacrylic acid and esters thereof, e.g., methacrylate, methyl methacrylate, etc.; vinyl aromatic monomers, e.g., styrene, α-methyl styrene, etc; vinyl acetate; vinyl alcohol; vinylidene chloride; acrylonitrile and substituted derivatives thereof; methacrylonitrile and substituted derivatives thereof; acrylamide and methacrylamide and N-substituted derivatives thereof; vinyl chloride, crotonic acid and esters thereof; etc. Again, it is noted that such optional copolymerizable vinyl monomer can comprise any conventional vinyl monomer copolymerizable with N-vinyl pyrrolidone.

Accordingly, the quaternized copolymers employed in the novel compositions of the present invention can be characterized as having a repeating structural unit derived from A. 40 – 90 mole % of vinyl pyrrolidone;
B. 5 – 40 mole % of a di-loweralkylaminoalkyl acrylate or methacrylate of a di-loweralkylaminohydroxyalkyl acrylate or methacrylate and C. 0 – 50 mole % of a vinyl monomer copolymerizable with vinyl pyrrolidone.

Such copolymers are conveniently prepared by subjecting a solution of vinyl pyrrolidone and the amino acrylate or amino methacrylate monomer with or without an optional copolymerizable vinyl monomer to conditions conducive to vinyl polymerization through the double bond. Thus, for example, polymerization may suitably be initiated by the action of free radicals, the polymerization proceeding exothermically once initiated. Suitable free radical catalysts conveniently employed and suitably utilized in accordance with the production of the copolymers include organic and inorganic peroxides, e.g., hydrogen peroxide, t-butyl peroxide, etc., aliphatic azo compounds, e.g., azobisisobutyronitrile as well as other free radical forming catalysts well known in the polymerization art.

The polymerization is preferably carried out in solution at temperatures varying from about 50° C to 100° C or more; however, to avoid run away conditions and to obtain a copolymer of a desirable molecular weight it is sometimes preferred to carry out the copolymerization at a temperature of from about 75° to about 85°C. The copolymerization reaction is preferably carried out in the absence of free oxygen, conveniently under a blanket of an inert gas, such as, nitrogen, argon or the like, or at atmospheric pressure.

As indicated previously the copolymers are in the form of their quaternary salts. Accordingly, after completion of the polymerization reaction the polymer is submitted to a treatment conductive to quaternization of the tertiary amino group, utilizing a conventional quaternizing agent. Thus, noting the above structural formula for the copolymers, suitable quaternizing agents include, such as, dialkyl sulfates, e.g., dimethyl sulfate, diethyl sulfate, etc.; alkyl sulfonic acid, e.g., methyl sulfonic acid, ethyl sulfonic acid, etc.; benzyl halides, e.g., benzyl chloride, benzyl bromide, benzyl iodide, etc.; alkyl halide, etc. Accordingly, any conventional quaternizing agent can be advantageously employed in the production of the quaternary N-vinyl pyrrolidone copolymers used in the cosmetic compositions of the present invention.

The above copolymers employed in the compositions of the present invention can be prepared over a wide range of molecular weights. Generally, however, the molecular weight of the copolymer employed in the novel composition of the present invention is within the range of 15,000 to 1,000,000, the molecular weight being chosen somewhat with respect to the utility of the cosmetic composition. In this regard, the copolymers of the present invention are soluble in both water and alcohol and, thus, can be employed in hair spray and similar cosmetic compositions containing an alcoholic, aqueous, or mixed alcoholic-aqueous base. In addition, the high molecular weight quaternary polymers act as their own thickeners in aqueous or alcoholic solutions, such solutions displaying a slippery feel and an ease of application to the hair. Accordingly, the use of such higher molecular weight quaternary copolymers, i.e., quaternary copolymers within the molecular weight range of 50,000 to 500,000 is particularly applicable to the preparation of hair setting lotions, creams, etc.

A further advantage of the use of the quaternary copolymers in the hair setting and similar cosmetic preparations is that hair sprayed or otherwise treated with a hair setting composition containing the quaternized copolymers is easy to comb and easy to roll on rollers. In addition, setting and conditioning lotions prepared utilizing the quaternary copolymers give a firm and stiff curl yet allow easy combing without comb drag.

As indicated above, since the quaternary copolymers employed in the novel compositions of the present invention are soluble in both alcohols and water, this makes such copolymers eminently suitable in hair spray and similar compositions which conventionally have an alcoholic, aqueous, or mixed aqueous-alcoholic base. Thus, the quaternary copolymers can be employed in the same manner as heretofore employed conventional film-forming resins, such copolymers providing improvements as set forth above by their inclusion within the hair spray, setting lotion, or similar cosmetic preparation.

In the compositions of the present invention the film-forming quaternary copolymer of N-vinyl pyrrolidone is generally employed in an amount of from about 0.1% to about 35% by weight, the precise amount depending somewhat on the end desired utility for the composition. In addition, it is pointed out that for particular purposes it may be desirable to employ slightly less or greater amounts of the film-forming polymer, here again, the end use of the composition dictating the precise amount employed in the novel compositions of the present invention.

As indicated above, for hair spray compositions, the base can either be aqueous, alcoholic, or a mixture of alcohols and water. The alcohol which is used as the alcoholic base or portion of the water-alcohol solvent system is generally a lower monohydric aliphatic alcohol, preferably, a monohydric aliphatic alcohol having from 2 to 3 carbon atoms, e.g., ethanol, isopropanol, or n-propanol, ethanol being preferred. Thus, for example, the alcoholic solvent can comprise the commercially and industrially available ethyl alcohols or any one of the denatured alcohol formulas which are permitted by law for use in hair spray preparations, i.e., any one of those listed for this use in "Formulas for Denatured Alcohol," Part 212, Title 26 CFR, IRS publication 368. Representative formulas having current approval that can be used are, for example: SDA-40 which consists of 100 gallons of ethyl alcohol denatured with 1.5 oz. of brucine sulfate and one-eighth gallon of tertiary butyl alcohol; SDA-23 A which consists of ten gallons of acetone in each one hundred gallons of ethyl alcohol; annd SDA-23 H which consists of eight gallons of acetone and one and one half gallons of methyl isobutyl ketone in each one hundred gallons of ethyl alcohol.

In addition to the film-forming quaternary copolymer and the solvent present in the system the hair spray or similar composition may contain minor amounts of other ingredients for their usual purposes. Thus, for example, the compositions may include wetting agents, defoamers, antibiotic agents, perfumes, coloring materials, and the like additives which are soluble in the aqueous, alcoholic, or mixed solvent medium.

In addition, the hair spray or similar composition may contain a suitable plasticizer for the novel quaternary copolymer employed as the film-forming resin. In this regard, the liquid substantially non-volatile polyols have been found particularly useful. Such materials include such as polyethylene glycols and ethylene oxide derivatives of monohydric alcohols, i.e., the ethylene oxide derivative of isostearyl alcohol.

In addition, when the aqueous, alcoholic, or mixed solvent system containing the quaternary copolymer film-forming resin is utilized as a spray formulation the usual aerosol type container and equipment and usual aerosol type propellant may be effectively utilized. Thus, the propellant may be any material which can be suitably utilized to propel compositions on the hair, such propellants being liquidified lower hydrocarbons such as propane, N-butane, and isobutane and the low boiling chlorofluoro hydrocarbons identified broadly as freons. Thus, for example, mention is made of freon 11-trichlorofluoromethane, freon 12-dichlorodifluoromethanae and freon 114 - 1,2-dichloro-1,1,2,2,-tetrafluoroethane.

In an aerosol type hair spray composition in accordance with the present invention the propellant is generally employed in an amount of from about 25 to about 65% by weight based on the total composition. The film-forming quaternary copolymer constitutes from about 0.1 to about 5% by weight with the remainder constituting the alcohol, water, or water-alcohol mixture. In addition, the hair spray composition can contain minor amounts, i.e., up to about 5% by weight of a surfactant or plasticizer and still lesser amounts of perfumes, i.e., up to about 0.5% by weight and similar agents.

In accordance with the preferred embodiment of the present invention, the sprayable hair composition is generally formed as an alcoholic or mixed aqueous-alcoholic solvent system. Accordingly, suitable amounts of the various components in such composition are as follows:

| Component | Amount |
| --- | --- |
| Quaternary film-forming resin | 0.1 – 5% |
| alcohol | 30 – 70% |
| propellant | 25 – 65% |
| water | 0.25% |

With respect to the above formulation, it is again pointed out that the use of the solvent system and propellant is conventional in the aerosol hair spray art, the improvement in accordance with the present invention residing in the use of the particular film-forming quaternary copolymer of N-vinyl pyrrolidone.

Improved setting and conditioning lotions for the hair can also be provided by the employment of a minor amount, i.e., 0.1 –5% by weight of the film-forming quaternary copolymer of N-vinyl pyrrolidone in an aqueous or mixed aqueous and alcoholic system. Accordingly, in accordance with the present invention such a setting and conditioning lotion may comprise the following components:

| Component | Amount |
|---|---|
| Film-forming quaternary copolymer | 0.1 – 5% |
| Water | 60 – 95% |
| Alcohol | 0 – 35% |

With respect to such setting and conditioning lotions, it is again pointed out that it is preferred in accordance with the present invention to employ the higher molecular weight quaternary copolymers of N-vinyl pyrrolidone. In this regard, when employing the higher molecular weight copolymers in the aqueous or mixed aqueous-alcoholic solvent system such copolymers act as their own thickeners thereby providing a creamy lotion consistency to the composition. This is true even when employed in a minor amount of 0.1 –5% by weight as set forth above.

As was the case with respect to the aerosol hair spray compositions, the setting and conditioning lotions may contain minor amounts of other conventional optional materials. These include such materials as perfumes, preservatives, additional organic solvents, lanolin and lanolin derivatives, silicone lubricity agents, etc. Here again, all of these optional components are conventional and employed in minor amounts, i.e., less than about 2% by weight. An optional surfactant or plasticizer for the film-forming copolymer can also be employed in an amount up to about 5% by weight.

In addition to the hair preparations, i.e., aerosol hair sprays and setting and conditioning lotions, the cosmetic compositions of the present invention can take the form of creams, particularly protective hand creams. Here again, such improved cosmetic compositions can be obtained by employing the film-forming quaternary copolymers of N-vinyl pyrrolidone in lieu of conventional film-forming resins.

In addition to the hair sprays and setting and conditioning lotions, it should be clear that the use of the film-forming quaternary copolymer of N-vinyl pyrrolidone in accordance with the present invention can provide for advantageous results in many similar cosmetic and related compositions wherein film-forming resins are utilized. Thus, for example, compositions can be prepared in the form of wig conditioners, hair coloring preparations, hand lotions, protective creams, moisturizing creams, anti-flash creams, deodorant sprays, cream rinses and shampoos as well as pet shampoos and industrial compositions such as sanitizer solutions, detergents, paper adhesive additives, carriers for pigments in printing inks, stencil inks, etc. Here again, it has been found that the use of the film-forming quaternized copolymer of N-vinyl pyrrolidone provides for results not heretofore obtainable with the use of conventional film-forming resins.

Thus, for example, it is possible to provide a protective water-repellent hand cream by employing the quaternized copolymer of N-vinyl pyrrolidone in accordance with the present invention. Thus, for example, a suitable cream which can be dispensed as a heavy foam can comprise an alcoholic solution of the film-forming copolymer, water, emollients, and an aerosol propellant with or without other conventional additives. Thus, for example, a suitable composition can comprise water, ethanol, the film-forming copolymer and emollients such as glycerine and derivatives, fatty acids and esters thereof, lanolin and derivatives thereof, silicones and mixtures of the above. Here again, in such a hand cream composition the use of the quaternized copolymer of N-vinyl pyrrolidone in accordance with the present invention is seen to provide substantially better result than the use of conventional film-forming polymers. Here again, such quaternized copolymer should be employed in an amount from about 0.1 to 5% by weight, the alcoholic solvent in an amount of up to about 10% by weight, the water solvent in an amount from about 50 – 90% by weight, the propellant in an amount from about 15 – 45% by weight and the various emollients in an amount from about 10 – 40% by weight.

As indicated previously, the film-forming quaternary copolymers of N-vinyl pyrrolidone are soluble in both the alcoholic and aqueous systems utilized in the preparation of the above and similar cosmetic and related preparations. Accordingly, in order to produce such formulations, it is merely necessary to dissolve the copolymer in the suitable solvent with previous, simultaneous or subsequent addition of the other optional components. Solution of the copolymer in the solvent system may be facilitated by mixing.

The novel compositions of the present invention will be illustrated by reference to the following specific examples.

EXAMPLE 1

Production of film-forming quaternary copolymer

A copolymer was produced utilizing polymerization apparatus comprising a 5 liter kettle equipped with mechanical stirrer, reflux condenser, thermometer, and gas inlet tube. Some 1,225 parts of ethanol as a solvent were charged into the kettle and 800 parts of vinyl pyrrolidone and 200 parts of dimethylaminoethyl methacrylate were added and agitation was started. To the system was added one part of azobisisobutyronitrile and the system was purged thoroughly with nitrogen. The temperature of the system was raised to gentle reflux at about 85° C.

The polymerization reaction was promoted with further additions of catalysts (one part each) until the amount of residual monomer was below 0.6%. The system was thereafter cooled to 25° C and the speed of the agitation was increased.

In order to provide the quaternary derivative of the copolymer 98.3 parts of diethyl sulfate were added from a dropping funnel over a period of 30 minutes. When the slightly exothermic reaction of quaternization was completed the mixture was agitated for an additional period of thirty minutes. An analysis of the product produced indicated that the same contained 49.19% solids with the residual monomer content being 0.57%. The K value of the copolymer was 74.8, the same having a relative viscosity as measured as a 1% solution in ethanol of 2.837, and an intrinsic viscosity of 1.25 and a Brookfield viscosity of 26,000 cps.

EXAMPLE 2

An aerosol hair spray composition was produced by admixing the following components in the weight percent indicated

| | Weight % |
|---|---|
| Low molecular weight vinyl pyrrolidone/dimethylaminoethyl methacrylate copolymer (80:20) quaternized with diethyl sulfate (50% solids in $H_2O$) and produced in Ex. 1 | 4.00 |
| Isostearyl alcohol plus 3 E. O. | 0.10 |
| Silicon SF-1075 (Gen. Elec.) | 0.05 |
| Perfume | 0.05 |
| Alcohol SD-40 anhydrous | 35.80 |
| Propellants trichlorofluoromethane and dichlorodifluoromethane 65:35 ratio | 60.00 |
| | 100.00 |

The aerosol hair spray formulation was prepared by dissolving the film-forming copolymer in the ethanol solvent and thereafter adding the plasticizer with vigorous mixing. After such mixing the perfume oil was added and the composition filtered and transferred to an aerosol can where it was crimped and charged with the necessary propellants.

Such a hair spray composition was found to be easily applied to the hair, the same providing a natural look yet offering excellent holding power. The stiff look associated with the use of half esters of polyvinyl ethers, maleic anhydride or polyvinyl acetate, crotonic acid co- and terpolymer hair setting resins was not present and there appeared to be no flaking associated with the employment of the hair spray composition containing the film-forming quaternary copolymer of N-vinyl pyrrolidone.

EXAMPLE 3

In a manner similar to Example 2 an aerosol hair spray, particularly adapted for men was prepared in an alcohol-aqueous solvent system. Utilizing a mixing procedure as in Example 2, the following composition was prepared

| | Weight % |
|---|---|
| Low molecular weight vinyl pyrrolidone/dimethylaminoethyl methacrylate copolymer (80:20) quaternized with diethyl sulfate (50% solids in alcohol) and produced in Example 1 | 4.00 |
| Isostearyl alcohol plus 3 E. O. | 0.65 |
| Perfume oil | 0.10 |
| Water deionized | 15.00 |
| Alcohol SD-40 anhydrous | 50.25 |
| Propellant - $CCl_2F_2$ and $CClF_2CClF_2$ 50:50 mixture | 30.00 |
| | 100.00 |

As was the case with respect to Example 2, the hair spray composition was found to have excellent holding properties providing a natural look to the hair. Here again, the use of the quaternized copolymer of N-vinyl pyrrolidone was seen to be superior to other conventional film-forming resins in that no flaking and no undue stiffness of the hair resulted.

EXAMPLE 4

A composition as in Example 3 was prepared except that the film-forming quaternized copolymer of N-vinyl pyrrolidone and dimethylaminoethyl methacrylate was replaced with a substantially equivalent amount of a quaternized copolymer of N-vinyl pyrrolidone and the following monomers:
 a. dimethylaminomethyl acrylate
 b. dimethylamino-2-hydroxypropyl acrylate
 c. diethylamino-2-hydroxyethyl methacrylate
 d. dimethylaminobutyl acrylate
 e. diethylaminooctyl acrylate
 f. diethylaminolauryl methacrylate
 g. diethylaminostearyl methacrylate When the copolymers produced are employed as the film-forming resin in a hair spray composition such as set forth in Example 3, substantially equivalent results are obtained.

EXAMPLE 5

A hair spray composition as set forth in Example 2 was produced except that the quaternized copolymer of N-vinyl pyrrolidone was prepared by employing the following comonomers in the following amounts:
 a. 800 parts of vinyl pyrrolidone - 100 parts dimethylaminoethyl methacrylate
 b. 800 parts vinyl pyrrolidone - 300 parts dimethylaminoethyl acrylate
 c. 800 parts vinyl pyrrolidone - 500 parts dimethylamino ethyl acrylate
 d. 800 parts vinyl pyrrolidone - 600 parts dimethylaminoethyl acrylate.

Here again, such quaternized copolymers of N-vinyl pyrrolidone are found to be eminently suitable in hair spray compositions in that compositions having excellent characteristics are obtained.

EXAMPLE 6

A hair spray composition as set forth in Example 2 was again produced except that the quaternized copolymer of N-vinyl pyrrolidone was one produced by the copolymerization system of Example 1 including the following further copolymerizable vinyl monomers:
 a. Methylvinylether - 100 parts
 b. octylvinylether - 200 parts
 c. methacrylic acid - 150 parts
 d. methyl methacrylate - 300 parts
 e. styrene - 200 parts
 f. vinyl acetate - 100 parts
 g. vinylidene chloride - 100 parts - vinyl chloride - 100 parts
 h. methacrylonitrile - 300 parts When the quaternized copolymers produced are employed in the hair spray composition of Examaple 2 in substantially equivalent amounts it is found that hair spray compositions of substantially equivalent properties are provided.

EXAMPLE 7

An anhydrous aerosol hair spray was produced through a procedure such as set forth in Example 2 by combining the following components:

| | Weight % |
|---|---|
| Low molecular weight vinyl pyrrolidone/dimethylaminoethyl methacrylate copolymer (80:20) quaternized with diethyl sulfate and produced in Example 1 50% solution in ethanol | 4.00 |
| Isostearyl alcohol plus 3 E. O. | 0.50 |
| Perfume oil | 0.10 |
| Alcohol SD-40 anhydrous | 50.40 |
| Methylene chloride | 15.00 |
| Propellants trichloroflouromethane and dichlorodifluoromethane 50:50 mixture | 30.00 |

-continued

| | Weight % |
|---|---|
| | 100.00 |

The above composition containing no water was also found to be extremely suitable for hair spray purposes. In this regard, the composition containing the quaternized copolymer exhibited excellent adhesion and holding power when employed as an aerosol hair spray, particularly adapted for men.

EXAMPLE 8

A setting and conditioning lotion for women's hair was produced as follows. A high molecular weight copolymer of vinyl pyrrolidone and dimethylaminoethyl methacrylate (80:20) quaternized with diethyl sulfate was dissolved in water and alcohol so as to provide a 2.0% solids content. After mixing the system well, a plasticizer, silicone lubricity agent, and perfume oil were added with additional mixing. Stirring was stopped and the system was allowed to rest for about 20 minutes so as to allow the escape of air bubbles. Such a formulation designed for use on damp or towel dried hair can then be packed in a plunger or tube type dispenser. The composition produced as above had the following formulation:

| | Weight % |
|---|---|
| High molecular weight vinyl pyrrolidone dimethylaminoethyl methacrylate copolymer (80:20) quaternized with diethyl sulfate (21.9% solids in H$_2$O) | 9.10 |
| Isostearyl alcohol plus 10 E. O. | 0.10 |
| Silicone Fluid SF-1066 (GE) | 0.10 |
| Perfume Oil | 0.05 |
| Alcohol SD-40 | 20.00 |
| Water deionized | 70.65 |
| Preservative | q.s. |
| | 100.00 |

EXAMPLE 9

In a manner similar to Example 8, a setting and conditioning lotion was prepared from the following formulation:

| | Weight % |
|---|---|
| High molecular weight vinyl pyrrolidone dimethylaminoethyl methacrylate (90–10 copolymer) quaternized with diethyl sulfate (21.9% solids in H$_2$O) | 9.10 |
| Isostearyl alcohol plus 10 E. O. | 0.10 |
| Partially acetylated lanolin derived complex | 0.10 |
| Perfume and preservative | q.s. |
| Water deionized | 90.70 |
| | 100.00 |

Here again, the above components provide a setting and conditioning lotion having advantageous properties associated with the use of the copolymer of vinyl pyrrolidone and dimethylaminoethyl methacrylate.

EXAMPLE 10

The following example illustrates the preparation of a water-repellant protective hand cream produced through the use of a quaternized copolymer of N-vinyl pyrrolidone in accordance with the present invention.

The composition was produced in four parts, Part A comprising the solution of quaternized copolymer, Part B comprising the emollients and various optional additives, Part C comprising a perfume, and Part D comprising the propellant.

In the preparation of Part A, the low molecular weight copolymer of vinyl pyrrolidone and dimethylaminoethyl methacrylate (80:20) quaternized with diethyl sulfate was mixed with ethanol, water, and glycerine until all of the copolymer was in solution. Part A, therefore, constituted the following components:

| | Parts by wgt. |
|---|---|
| Low molecular weight vinyl pyrrolidone/dimethylaminoethyl methacrylate copolymer (80:20) quaternized with diethyl sulfate and produced in Example 1 50% solution in ethanol | 6.4 |
| Glycerin | 10.0 |
| Water deionized | 876.6 |

Part B was prepared by mixing the following components:

| | |
|---|---|
| Isopropyl Myristate | 15.0 |
| Stearic acid | 35.0 |
| Triethanolamine | 8.2 |
| Cetyl alcohol | 4.8 |
| Silicone SF-1075 (Gen. Electric Co.) | 15.0 |
| Acetylated lanolin alcohol | 5.0 |

Parts A and B were separately mixed and heated to 160° – 165° F. Thereafter, the aqueous system of Part A was added to Part B with vigorous mixing, the composition slowly cooled and Part C, 0.3 parts by weight of perfume added. 85 parts of the emulsified product were then transferred to an aerosol can and crimped with the can being filled to suitable pressure with 15 parts of the propellants of Part D, i.e., Propellant - CCl$_2$F$_2$ and CClF$_2$CClF$_2$ (50:50).

The above composition which is dispensed as a heavy foam is found to be particularly suitable as a protective hand cream, the same having excellent film-forming properties and protective properties associated with the employment of the quaternized copolymer of N-vinyl pyrrolidone.

It can be clearly seen from the above that the objects and advantages of the novel compositions of the present invention are achieved through the employment of a film-forming quaternized copolymer of N-vinyl pyrrolidone in lieu of conventional film-forming resins utilized in cosmetic compositions, principally compositions adapted for use on the hair.

Thus, the hair sprays of the present invention are seen to provide excellent adhesion and holding power without the disadvantages of previously employed compositions.

What is claimed is:

1. A hair-setting and hair-conditioning composition comprising a solvent base selected from the group consisting of water, monohydric C$_{2-3}$ aliphatic alcohols, and mixtures thereof, containing approximately by weight 0.1 to 35% of a film-forming quaternized polymer having a molecular weight ranging from 15,000 to 1,000,000 and having the formula:

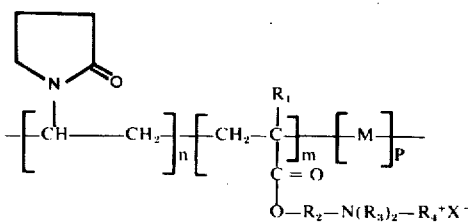

wherein n is 40–90 mole percent, m is 5–40 mole percent, p is from 0–50 mole percent and $n+m+p = 100$ mole percent;

$R_1$ is selected from the group consisting of H and $CH_3$;

$R_2$ is $C_xH_{2x}$ where $x = 2-18$; $R_3$ is selected from the group consisting of $CH_3$ and $C_2H_5$; $R_4$ is selected from the group consisting of $CH_3$, $C_2H_5$, and

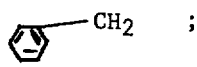

X is selected from the group consisting of Cl, Br, I, $SO_4$, $HSO_4$, and $CH_3SO_3$; and M is a monovinyl monomer different from and copolymerizable with the other monomeric units of said polymer.

2. A composition as defined in claim 1 wherein the quaternized component of said quaternized polymer is derived from a precursor selected from the group consisting of dimethylaminomethyl acrylate, dimethylaminomethyl methacrylate, diethylaminomethyl acrylate, diethylaminomethyl methacrylate, dimethylaminoethyl acrylate, dimethylaminoethyl methacrylate, dimethylaminobutyl acrylate, dimethylaminobutyl methacrylate, dimethylaminoamyl methacrylate, diethylaminoamyl methacrylate, dimethylaminohexyl acrylate, diethylaminohexyl methacrylate, dimethylaminooctyl acrylate, dimethylaminooctyl methacrylate, diethylaminooctyl acrylate, diethylaminooctyl methacrylate, dimethylaminodecyl methacrylate, dimethylaminododecyl methacrylate, diethylaminolauryl acrylate, diethylaminolauryl methacrylate, dimethylaminostearyl acrylate, dimethylaminostearyl methacrylate, diethylaminostearyl acrylate and diethylaminostearyl methacrylate; and the monomer M is selected from the group consisting of alkyl vinyl ethers; acrylic and methacrylic acid and esters thereof; vinyl aromatic monomers; vinyl acetate; vinyl alcohol; vinylidene chloride; acrylonitrile and substituted derivatives thereof; methacrylonitrile and substituted derivatives thereof; acrylamide and methacrylamide and N-substituted derivatives thereof; vinyl chloride and crotonic acid and esters thereof.

3. A hair setting and conditioning lotion containing the composition as defined in claim 2.

4. The hair setting and conditioning lotion of claim 3 wherein said film-forming quaternized polymer is a copolymer of vinyl pyrrolidone and dimethylaminoethyl methacrylate.

5. A hair cream containing the composition as defined in claim 2.

6. An aerosol hair spray containing an effective amount of an alcohol and a composition as defined in claim 2, 7. An aerosol hair spray containing approximately by weight 25 to 65% of a propellant and 75 to 35% of a composition as defined in claim 6.

8. An aerosol hair spray composition comprising:
  a. 30 – 70% by weight of said monohydric $C_{2-3}$ aliphatic alcohol as solvent;
  b. 0 – 25% by weight of water;
  c. 25 – 65% by weight of an aerosol propellant; and
  d. 0.1 – 5% by weight of said film-forming quaternized polymer.
as defined in claim 6.

9. A hair setting and conditioning lotion comprising:
  a. 60 – 95% by weight of water;
  b. 0 – 35% by weight of said $C_{2-3}$ monohydric aliphatic alcohol; and
  c. 0.1 – 5% by weight of said film-forming quaternized polymer
as defined in claim 3.

10. An aerosol hairspray as defined in claim 6 wherein the quaternized component of said quaternized polymer is derived from a precursor selected from the group consisting of dimethylaminoethyl methacrylate, dimethylaminomethyl acrylate, dimethylaminobutyl acrylate, diethylaminooctyl acrylate, diethylaminolauryl methacrylate, and diethylaminostearyl methacrylate.

11. A hair-setting composition as defined in claim 3 wherein the quaternized component of said quaternized polymer is derived from a precursor selected from the group consisting of dimethylaminoethyl methacrylate and dimethylaminoethyl acrylate and is the monomer M selected from the group consisting of methyl vinyl ether, octyl vinyl ether, methacrylic acid, methyl methacrylate, styrene, vinyl acetate, vinylidene chloride, vinyl chloride, and methacrylonitrile.

12. The composition of claim 2 wherein the quaternized component is derived from a precursor of dimethylaminoethyl methacrylate.

13. The composition of claim 7 wherein the quaternized component is derived from a precursor of dimethylaminoethyl methacrylate.

* * * * *